(12) United States Patent
Andersson et al.

(10) Patent No.: US 6,607,386 B1
(45) Date of Patent: Aug. 19, 2003

(54) METHOD AND DEVICE FOR, AND USE OF, A DENTAL PRODUCT

(75) Inventors: Matts Andersson, Lerum (SE); Elis Carlstrom, Gothenburg (SE); Mikael Eriksson, Gothenburg (SE)

(73) Assignee: Nobel Biocare AB, Gothenburg (SE)

( * ) Notice: Subject to any disclaimer, the term of this patent is extended or adjusted under 35 U.S.C. 154(b) by 0 days.

(21) Appl. No.: 09/786,918

(22) PCT Filed: Sep. 8, 1999

(86) PCT No.: PCT/SE99/01559

§ 371 (c)(1),
(2), (4) Date: Jul. 5, 2001

(87) PCT Pub. No.: WO00/15137

PCT Pub. Date: Mar. 23, 2000

(30) Foreign Application Priority Data

Sep. 11, 1998 (SE) .............................................. 9803075

(51) Int. Cl.⁷ .................................................. A61C 5/10
(52) U.S. Cl. .................................................. 433/201.1
(58) Field of Search ........................ 433/201.1, 223, 433/207, 206, 218

(56) References Cited

U.S. PATENT DOCUMENTS

| | | | | |
|---|---|---|---|---|
| 4,661,071 A | * | 4/1987 | Bell et al. ................... | 433/223 |
| 4,828,495 A | * | 5/1989 | Bell et al. ................. | 433/201.1 |
| 5,073,113 A | * | 12/1991 | Hornig ........................ | 433/223 |
| 5,318,746 A | * | 6/1994 | Lashmore et al. .......... | 433/223 |
| 5,342,201 A | * | 8/1994 | Oden .......................... | 433/223 |
| 5,775,912 A | * | 7/1998 | Panzera et al. ............. | 433/223 |
| 5,852,248 A | * | 12/1998 | Chadwick ................... | 433/207 |
| 6,354,836 B1 | * | 3/2002 | Panzera et al. ............. | 433/223 |

* cited by examiner

*Primary Examiner*—Todd E. Manahan
(74) *Attorney, Agent, or Firm*—Connolly Bove Lodge & Hutz LLP

(57) ABSTRACT

A dental product is produced from material in powder form. In a first manufacturing stage, the product is given a shape which is larger than its final shape, and in further manufacturing stages the product is subjected to material shrinkage, sintering and working in order to obtain its final shape. Metal powder is applied to the mold tool, and the mold tool with the applied metal powder is placed in pressure-generating equipment where the powder applied to the mold tool is subjected to compaction pressure which compacts the powder so that at least 80% basic density is obtained in the material. The compacted material is then machined. After machining, the compacted material is removed from the mold tool. The sintering stage is then carried out so that the final shape is obtained.

30 Claims, 2 Drawing Sheets

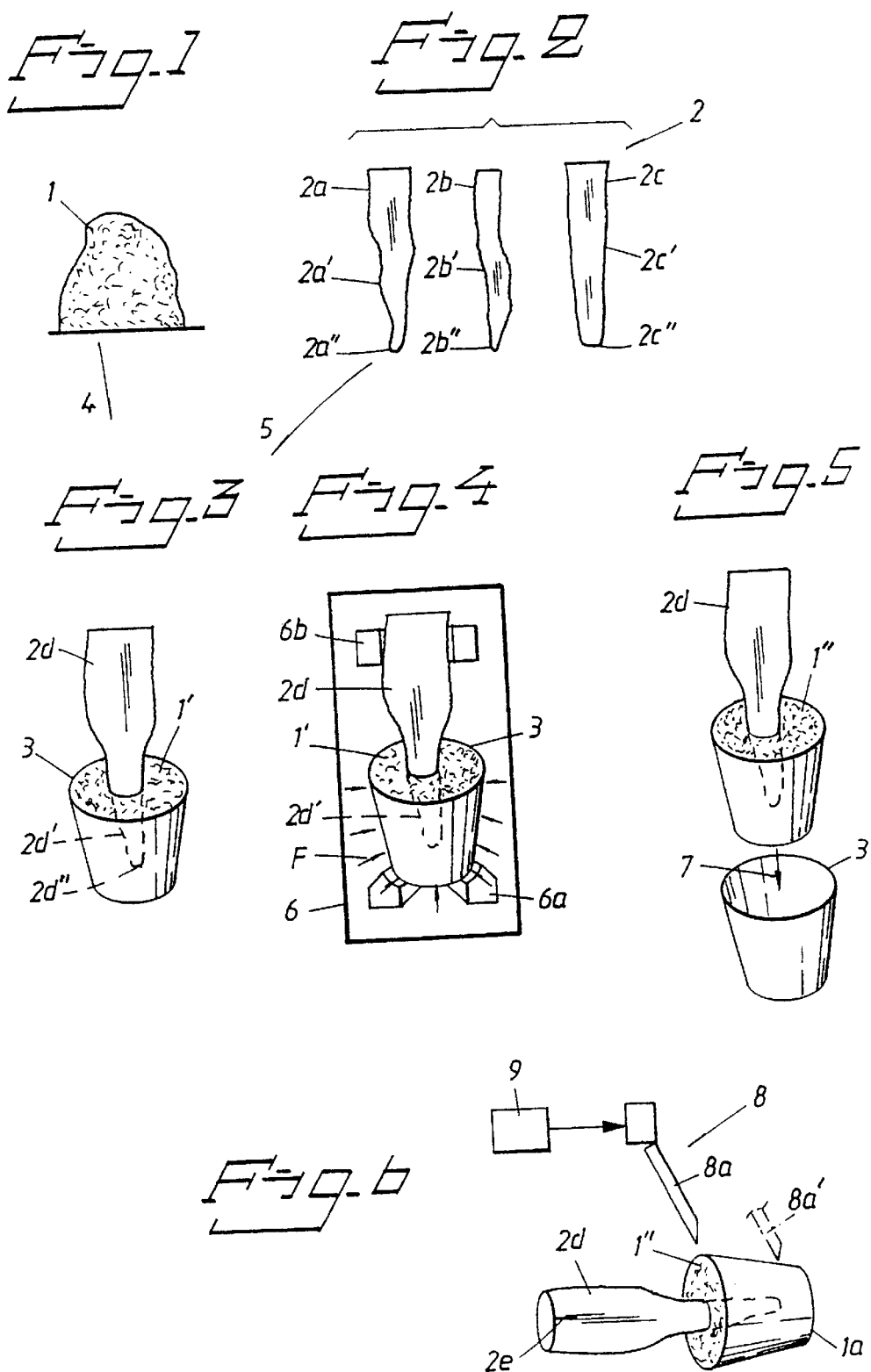

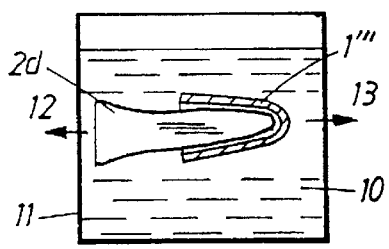
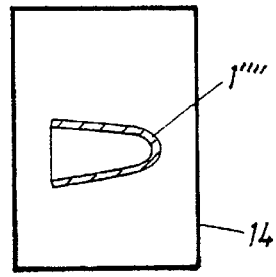
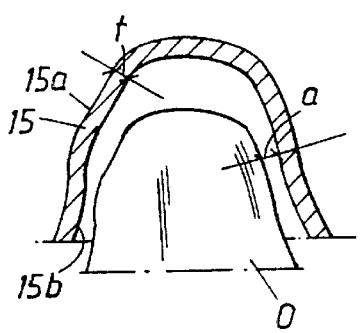
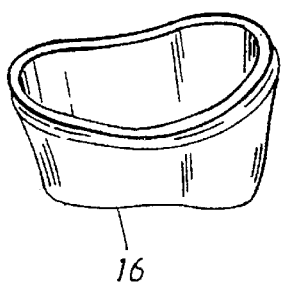
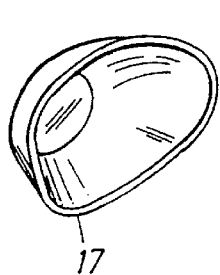
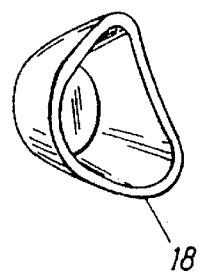

METHOD AND DEVICE FOR, AND USE OF, A DENTAL PRODUCT

TECHNICAL FIELD

The present invention relates to a method for producing a dental product or other product for the human body using material in powder form. In a first manufacturing stage, with the aid of a mould tool, the product is given a shape which is larger than its final shape, and in further manufacturing stages the product is subjected to working and material shrinkage/sintering to obtain the final shape. The invention also relates to a product intended as a component in a dental application or other application in the human body, where it cooperates with members in the form of implants, attachment parts for implants, bones, for example dentine, tooth remnants, etc. The product is made up from worked and sintered and worked powder material. The invention also relates to a use of the product of the said type.

PRIOR ART

It is already known to make products or bodies of the type in question using powder material in the form of ceramic powder. In this context, it is known to use mould tools in which the ceramic powder is applied. The mould tool is given a larger shape or size. The ceramic powder is applied in the mould and is exposed to compression forces, after which the compressed body is worked and shrunk further in a sintering process.

Reference may be made in entirely general terms to manufacturing principles which are proposed and used in the Procera technique for manufacturing products of the type in question and where, inter alia, final outer shapes are produced from enlarged outer shapes.

Thus, from U.S. Pat. No. 5,192,173 (with the same inventor) it is already known to create a linearly enlarged shape on the tool in question. Reference is also made to European Patent 384,908 B1 same inventor) which shows that a linearly enlarged body can be subjected to a sintering process so as to be given its desired final shape.

It is also known to make products or bodies of the abovementioned type from metal. The outer shape of the product is in this case turned or milled from a blank. An electro-oxidation tool with an outer shape corresponding to the inner shape of the product is made and is used for producing the inner surface of the product by means of electro-oxidation.

DISCLOSURE OF THE INVENTION
TECHNICAL PROBLEM

The production of ceramic products and metal products has hitherto had to be carried out using two completely different techniques which have been employed within the technical area of dental technology and technology related to the human body. This has divided resources for manufacturers of these types of products and other products for the human body. There is a requirement for the technical resources to be brought together more effectively and, for example, for the same types of personnel to be used to produce caps, spacers, bridges, etc. The invention aims to solve this problem among others.

In the sector concerned with the manufacture of products, for example caps, made of metal material, consideration has been given to imitating the principles used for ceramic caps or equivalent. However, there has been strong technical opposition and considerable bias against its being possible, in serial manufacture of structurally robust caps/products which are to function in a technically severe environment (in the patient's mouth) and therefore must have strict strength requirements and at the same time upholding the precision requirements, to be able to manufacture caps/products in the same way as in ceramic production.

The invention counters this strong technical opposition and bias and takes a completely new approach in order to permit a new type of manufacture of caps/products of the type in question.

There is a need to technically simplify, and to make less expensive, the previous manufacture of caps and other dental products using mechanical working and electro-oxidation. The invention solves this problem too and now proposes principles in which previous strength and precision requirements (0.2 $\mu$m) can also be maintained.

In connection with the new principles for production of caps/products made of metal, there is a need to be able to vary the strength requirements, precision requirements, manufacturing process, etc. The invention solves this set of problems too and is not confined to individual procedures for achieving the requirements set. The new principles are especially suited to titanium powder which has the best biocompatible character. However, there have been strong doubts as to whether it is in principle possible to make caps and similar products from titanium powder material.

SOLUTION

The feature which can principally be regarded as characterizing a method according to the invention is that metal powder is applied to the mould tool, and that the mould tool with the applied metal powder is placed in pressure-generating equipment where the powder applied to the mould tool is subjected to compaction pressure which compacts the powder so that at least an 80 percent basic density is obtained in the material, and that thereafter the material compacted on the mould is first machined and then removed from the mould tool, after which the said material shrinkage/sintering stages are carried out so that the final shape is obtained, and at the same time a porosity of at most about 6 percent by volume, preferably at most 2 to 3 percent by volume, is obtained in the sintered product.

In one embodiment, the outer shape of the product is produced or worked (in an enlarged state), after which the product's final shape is obtained in the sintering process. The product is given a distinct or substantial homogeneity with respect to the distribution of the porosity. The material of the product is treated in such a way by the new method that it becomes ductile (substantially ductile) so that there is no tendency to crack or fracture under the effect of force.

In one proposed embodiment, the powder, on application to the mould tool in question, or stamp, is arranged in a powder-receiving unit in which the outer shape of the stamp can be lowered so that the powder surrounds the outer surface of the stamp. The powder can in this case be poured or applied into a tube-like or rubber bladder-like powder-receiving unit with elastic wall, which for example can be a silicone wall, via which the pressure is allowed to act in the pressure-generating equipment. The powder material chosen is preferably titanium powder which can comprise powder of the type TWC-f, whose particles are deformed by the compaction or the action of pressure in the pressure-generating equipment. The de-moulding of the compacted metal powder from the mould tool or stamp is preferably done in a bath of liquid nitrogen/air, and the stamp and the metal powder are in this case chosen with different coefficients of expansion, which means that the de-moulding is made considerably simpler. The sintering process in carried out in a vacuum sintering appliance.

In one embodiment, a number of mould tools or stamps which represent a number of possible unique or individual inner shapes of the product are produced. The respective stamp is selected from a selection of stamps depending on the inner shape which the product is to be given.

The metal powder material compacted on the mould tool or stamp is machined by turning or milling, the mould tool/stamp being arranged together with the compacted material. The product can in this case be given a shape with a cap-like character where the inner shape of the product corresponds to the outer surface of the mould tool/stamp, and the outer shape of the product is machined, for example by turning or milling. The turning or milling is preferably carried out from the upper part of the cap-like product and working downwards.

The mould tool/stamp is designed with a degree of enlargement which is preferably chosen within the range of enlargement immediately over 0% and up to about 12%, or immediately below 12%. The compaction pressure is chosen within the range of 300 to 900 MPa. The degree of enlargement used within the said range can be determined as a function of the compaction pressure used. The shrinkage or sintering operation provides a shrinkage or sintering which is slightly below the chosen degree of enlargement. The product is produced with inner or outer shapes produced with a degree of precision of about 20 $\mu$m. The product is preferably a thin-walled product, with values within the range of 400 to 600 $\mu$m. The product or the cap can also be produced with a precision which provides play of 100 to 400 $\mu$m in relation to the opposing surface of the dental member in question or the dental component in question.

Titanium powder is preferably used, but it is possible per se alternatively to use gold alloy or steel powder material.

The new product can principally be regarded as being characterized by the fact that the powder material consists of or comprises metal powder material deformed by compaction and sintered and having a porosity of at most 6, preferably 2 to 3, percent by volume.

The product is preferably (substantially) ductile and is (substantially) homogeneous and with evenly distributed porosity.

In a preferred embodiment, the product has essentially the shape of a cap. The product is thin-walled and can have a wall thickness or wall thicknesses within the range of 400 to 600 $\mu$m. The product has a precision fit on its inner and/or outer shapes of about 20 $\mu$m. The product or the cap forms a self-supporting structure or construction whose strength properties correspond to those of a conventional product for the dental application or other application in the human body. The product or the cap preferably has a degree of compaction which allows it to be worked by cutting tools, for example turning or milling, when producing the outer shape. The product consists or is made of titanium powder material in the first instance, although gold alloy or steel powder can alternatively be used.

A use of the product of the said type is characterized by the fact that metal powder which is compacted and sintered to a porosity of at most 6, preferably 2 to 3, percent by volume is used as powder material. Titanium powder is preferably used for producing a self-supporting product, for example cap.

ADVANTAGES

A surprising effect is that the strict precision requirements in accordance with the present case can be obtained with such a considerable degree of sintering of the metal powder, especially titanium powder, in question here.

The features which have been proposed above permit a considerably simplified manufacture of metal caps and products for dental application. Conventional press moulding and de-moulding principles as well as sintering principles can be used, so that technically simple and well—proven operations are possible. Tests carried out with respect to strength and precision show surprising effects in that the cap/product can be made at least as strong and accurately as caps/products produced using conventional techniques and by conventional methods. In addition, it is possible to control the manufacturing process so that discoloring of the product's surface(s) is eliminated. Particular advantages of the invention are obtained when titanium powder is used. Titanium powder can give strong, load-bearing products or caps.

DESCRIPTION OF THE FIGURES

A presently proposed embodiment of a method, device and use of the invention will be described below with reference to the attached drawings, in which FIG. 1 is a diagrammatic representation of the titanium powder used, FIG. 2 shows side views of parts of stamps which are included in a selection of stamps or tools, FIG. 3 shows in a perspective view, obliquely from above, a stamp chosen from the selection according to FIG. 2 and applied in powder according to FIG. 1, which powder is applied in a tube-shaped container, FIG. 4 is a perspective and diagrammatic representation of the components according to FIG. 3 introduced into compaction equipment, FIG. 5 is a perspective view of compacted powder adhering to the stamp in question, removed from the equipment according to FIG. 4, the container according to FIG. 3 being separated from the stamp and the compacted powder, FIG. 6 is a diagrammatic representation of the powder body and the stamp alongside or in machining equipment which is intended to give the metal powder body its outer shape, FIG. 7 is a diagrammatic side view showing the de-moulding function for the stamp and the worked powder body, FIG. 8 is a diagrammatic side view showing the worked powder body placed in a sintering oven, FIG. 9 shows, in a side view, an example of a structural design of a product/cap, FIGS. 10, 11 and 12 show, in different perspectives, three different caps produced according to the new method.

DETAILED EMBODIMENT

FIG. 1 shows diagrammatically a metal powder 1 which in the present case is a titanium powder, for example of the type TWC-f (Teledyn Wah Chang, where f stands for "fine") HDH 270 Mesh with a particle size of 53 $\mu$m. The powder is a so-called coarse powder (not granular).

FIG. 2 shows symbolically and partially a selection of mould tools 2, which are three in number and have been designated 2a, 2b, 2c. It is possible to have more stamps in the selection. Each stamp has a unique or individual outer shape 2a', 2b', 2c'. The surface of each stamp tapers towards the free end 2a'', 2b'', 2c'' of the stamp.

FIG. 3 shows a stamp 2d chosen from the selection 2 and having the same character as the other stamps, the outer surface having been designated by 2d' and the tip by 2d".
FIG. 3 shows an elastic container 3 which has the shape of
a tube-like unit or bladder which, in this example, is made
of silicone. The container or bladder can be filled with
powder 1' and the stamp 2d lowered into the powder (and/or
the bladder with the powder can be pushed onto the stamp)
with its said outer shape 2d', which is entirely surrounded by
the powder. The transfer of the powder has been symbolized
by 4 and the transfer of the stamp by 5 (FIGS. 1 and 2,
respectively).

The stamp 2d and container 3 with powder 1' have been
transferred to a heating oven 6 according to FIG. 4. The
combination of 2d and 3 is supported in the oven by support
members 6, 6b. The oven is of a type known per se and can
be a so-called ISOSTAT press which is sold commercially.
It is possible per se to use a special press which gives high
pressures. The pressure in the press can in one embodiment
vary from 300 MPa and upwards, for example to 900 MPa
or more, and in each case a working pressure is assumed
which is to be used for the product in question. As an
example, the work pressure has been chosen at 320 MPa.
The pressure used means that the powder 1' in the container
3 is pressed against the outer surface 2d' of the tool or stamp
by virtue of the elastic wall of the container 3, the press
forces being indicated by arrows F in FIG. 4. The pressure
can alternatively be exerted in one, two or more cycles. The
pressure can be successively increased over a certain period
of time. The pressure can be allowed to act on the powder
for a predetermined period of time, for example 15 minutes.
The pressure means that the powder is compacted to form a
powder body in which powder particles or corresponding
units are compacted in such a way that the particles or units
are deformed. The powder body is pressed with great force
against the outer surface 2d' of the stamp and comes to form
a common unit with the stamp. The combination of 1', 2d
and 3 can in turn be enclosed in a rubber covering (not
shown) in order for the powder to be held in place. The
covering can be a rubber balloon. The pressure treatment or
compaction of the powder body means that it is possible to
choose a basic density of the powder material of between
about 80% and about 90%, or a porosity of between about
10 and 20 percent by volume.

According to FIG. 5, the compacted powder body 1" with
attached stamp and container (or balloon) 3 is removed from
the oven 6. The container 3 or remains thereof (the balloon)
are removed from the powder body in the direction of arrow
7.

FIG. 6 shows a machining stage for producing and/or
treating the outer shape of the powder body 1". The machining equipment can be a turning lathe, milling device, etc.,
and has been symbolized by 8. The lathe bit or milling head
8a, 8a' has been shown in two positions. The machining
preferably starts at the free/outer end 1a of the powder body
and works downwards/inwards. This is done in order to
achieve the best possible function and, for example, to
prevent the cap from coming loose due to shiny and smooth
surfaces in cooperation during machining. The particle size
of the material of the stamp and cap can be included as
parameters in the machining. The outer shape formed on the
powder body 1' is controlled from a control function 9 which
controls the machining equipment 8. The control function is
already well known and will therefore not be described in
detail here. Sharp edges and corners can also be milled or
turned. Cooling agents, for example Medicway M15, are
used during machining in order to prevent unwanted effects
(discoloring) on the material in dry-milling or dry-turning.

FIG. 7 shows the de-moulding function for the product 1'''
which has been made and which, in the present case, has the
form of a cap. In a preferred embodiment, the de-moulding
is carried out using liquid nitrogen/air 10 in a container 11.
The nitrogen/air is at a temperature of about −180° C. The
stamp or tool 2d is in the present case made of material with
a higher coefficient of expansion than the titanium/powder
body. In this example, pure aluminium is chosen for the
stamp/tool having a coefficient of expansion of $25 \times 10^{-6 \circ}$
$C.^{-1}$. The titanium has a coefficient of expansion of $8.5 \times 10^{-6 \circ} C.^{-1}$. This therefore means that the stamp 2d shrinks
more than the powder body 1''' and that simple separation
can take place. The separation function is symbolized by
arrows 12, 13.

FIG. 8 shows the shrinkage or sintering function for the
enlarged shape 1''' for the product's final shape. The cap 1'''
is applied in an oven 14 which is a vacuum oven in which
sintering takes place and the cap 1'''' acquires its final shape.
The temperature in the vacuum oven 14 can be chosen at, for
example, between 800 and 1200° C., and the sintering is
carried out in one or more cycles with predetermined times,
for example times in the range of 2 to 4 hours/cycle. At the
start of the sintering process, the temperature can be
increased by 20° C. per minute until the predetermined
temperature is reached. The enlargement can be between
values immediately above 0% to about or immediately
below 12%. The cap 1''' is shrunk slightly less than the
chosen enlargement. Thus, for example, a shrinkage of 6.2%
may require an enlargement of 6.61%. The heat treatment/
sintering means that the density further increases and can
assume values of, for example, at least 94%, preferably 97
to 98%, which means a porosity of 6, preferably 2 to 3,
percent by volume. A product is thus obtained made of
sintered metal powder material and with the said low
porosity. The product is preferably substantially homogeneous over its entire extent and is characterized by high
ductility which prevents cracking and fracturing of the
material when it is exposed to forces arising in the dental
application or other application in the human body. Thus, for
example, impact tests were carried out on the product
obtained. Despite heavy hammer blows against the cap-like
product, there was no tendency for cracks to form in the
deformed area.

In a more detailed embodiment of the new method, an
aluminium stamp is milled with the correct tooth shape or
outer surface 2d' and is marked for re-positioning (see 2e in
FIG. 6) in order to facilitate the machining function. A
silicone rubber mould is made or re-used and the aluminium
stamp is entirely enclosed. In one embodiment, two silicone
rubber mould parts are used so that the whole combination
according to FIG. 3 for example is enclosed. Before this
enclosing, titanium powder is filled into the rubber mould,
cf. FIG. 3. The aluminium stamp is pressed down (by hand)
into the titanium powder and the second part of the rubber
mould can then be applied so that the whole combination
according to FIG. 3 is enclosed. The combination of aluminium stamp, titanium powder and rubber mould 3
enclosed in the balloon or mould according to FIG. 3 is
placed in the press according to FIG. 4, for example twice.
By means of this, the titanium sits firmly on the aluminium
stamp (which corresponds to the inner shape of the cap). The
components are then removed from the oven 6 and the
balloon and the rubber mould are removed from the metal
body and the aluminium stamp. The aluminium stamp is
re-positioned in the mill or turning lathe and the outer shape
of the titanium cap is milled or lathed. The titanium cap is
removed from the aluminium stamp in liquid nitrogen. The
titanium cap can then thaw, and condensed water vapour
evaporated off (dried). Penetrated cooling agent is released from the cap if this is necessary. The titanium cap is sintered on a molybdenum plate in vacuum with titanium (sacrificial titanium) present, which prevents discoloring. The titanium cap or equivalent product is then ready for inspection, measurement, shot-peening and continued working.

FIG. 9 shows a product 15 according to the invention. The product is thin-walled and can have a wall thickness t of 400 to 600 μm. In FIG. 9, the cap is shown in relation to a member O, which can be a tooth remnant, an implant, an attachment part for the implant, dentine, etc. In FIG. 9, the distance between the member and the inner surface 15b of the tooth cap is indicated by a. The cap 15 can be brought together with the member O so that a minimum gap arises, for example a gap of 100 to 400 μm. When the cap has been applied on the member, the inner surface adjoins the outer surface of the member with an intermediate gap. The outer surface 15a can in turn be adapted to a further component or components, for example in the form of a prosthetic construction.

FIG. 10 shows a sintered cap 16 which has been produced in accordance with the above and which is made of titanium powder TWC-f, pressed in a CIP press (Cold Isolate Pressure) with 450 MPa and sintered at 1200° C. for two hours. The surface structure is in this case chosen to be granular instead of smooth and the cap has a comparatively light (white) surface, which is important since it is not then necessary to conceal dark areas of the prosthesis. No brittle fractures or cracks occur. FIGS. 11 and 12 show two alternative embodiments of caps compared to the cap according to FIG. 10.

In one use of the invention, the powder used for the production is a metal powder which on the one hand is compacted so that deformation of the powder particles or equivalent occurs and a high degree of basic density, for example 80%, is obtained and, on the other hand, is sintered so that shrinkage to the final shape and accuracy occurs, the degree of density increasing further, for example to about 94%, preferably 97 to 98%, which gives a porosity of about 6, preferably 2 to 3, percent by volume. In a preferred embodiment, titanium powder is used.

The finished product obtained is preferably a cap with a cone-shaped or equivalent clearance which permits simple de-moulding in accordance with the above. Alternatively, a de-moulding method in the form of electro-oxidation can be used, which eliminates the stamp material.

As an alternative to titanium powder, it is possible to use powder of gold alloy, stainless steel, composite material of metal and/or ceramic powder. The pressure force, sintering time and sintering atmosphere can be adapted optimally to the different cases. The powder must have fine particles so that sintering can take place to the high density or low porosity. In cases where de-moulding with cooling in liquid nitrogen in accordance with the above cannot be used, it is possible to use de-moulding based on mechanical removal.

The invention is not limited to the embodiment given above by way of example, and instead can be modified within the scope of the attached patent claims.

What is claimed is:

1. A method for producing a dental product using titanium in powder form, where the product, in a first manufacturing stage, with the aid of a mould tool, is given a shape which is larger than a final shape of the product, and in further manufacturing stages is subjected to working and material shrinkage and sintering to obtain the final shape, comprising:

applying titanium powder to the mould tool;
   placing the mould tool with the titanium powder in pressure-generating equipment;
   subjecting the titanium powder to compaction pressure and thereby compacting the titanium powder so that a compacted powder body having at least an 80 percent basic density is formed;
   machining the compacted powder body and subsequently removing the compacted powder body from the mould tool; and
   after removing the compacted powder body from the mould tool, shrinking and sintering the compacted powder body into the final shape to form the dental product, wherein material of the dental product has a porosity of at most about 6 percent by volume in said final shape.

2. A method according to claim 1, wherein during compacting and machining of the titanium powder, the outer shape of the dental product is worked or produced, and wherein during sintering the dental product is given the final shape and material properties.

3. A method according to claim 1, wherein the material of the dental product is given a homogeneous and ductile structure.

4. A method according to claim 1, wherein the final shape and material properties are obtained using a CAD/CAM technique.

5. A method according to claim 1, wherein the mould tool is a stamp, and wherein the titanium powder, when applied to the stamp, is arranged in a powder-receiving unit in which an outer surface of the stamp can be lowered so that powder surrounds the outer surface of the stamp.

6. A method according to claim 1, wherein the titanium powder is poured or applied into a tube-like or rubber bladder-like powder-receiving unit with an elastic wall, via which the compaction pressure can act in the pressure-generating equipment, and wherein the mould tool, the powder-receiving unit and the titanium powder are in turn enclosed in an elastic covering.

7. A method according to claim 1, wherein removing the compacted powder body from the mould tool is done in a bath of nitrogen, and wherein a thermal coefficient of expansion of the mould tool exceeds the thermal coefficient of expansion of the titanium powder so that the compacted powder body is given a release function from the mould tool.

8. A method according to claim 1, wherein sintering comprises vacuum sintering.

9. A method according to claim 1, wherein the titanium powder is TWC-f with HDH 270 Mesh, 53 micrometers, whose particles are deformed by the action of pressure, and having particle sizes of 20 to 60 micrometers.

10. A method according to claim 1, wherein the product is produced with a degree of precision of about 20 μm wit respect to inner or outer shapes of the product.

11. A method according to claim 1, wherein the product has a wall thickness within the range of 400 to 600 μm or a gap size between an inner surface and an opposite surface of a dental component of 100 to 400 μm.

12. A method according to claim 1, wherein a number of mould tools representing a number of possible inner shapes of the product are provided, wherein the mould tools comprise stamps and a respective stamp is selected from among the stamps depending on an inner shape which the product is to be given.

13. A method according to claim 1, wherein the material compacted on the mould tool in the compaction stage is machined by turning or milling, the mould tool being arranged with attached compacted material.

14. A method according to claim 1, wherein the product is given a cap-like character where an inner shape of the product corresponds to an outer shape of the mould tool, and an outer shape of the product is machined by turning or milling.

15. A method according to claim 14, wherein the turning or milling is carried out from an upper part of the product working downwards.

16. A method according to claim 1, wherein the mould tool is designed with a degree of enlargement which is chosen within the range of enlargement immediately over 0% and up to or immediately below about 12%.

17. A method according to claim 16, wherein the degree of enlargement used within the range is determined as a function of the compaction pressure used, and wherein a low degree of enlargement is used for a low compaction pressure, and a high degree of enlargement is used for a high compaction pressure.

18. A method according to claim 16, wherein the shrinkage and sintering effect a shrinkage which is slightly below the chosen degree of enlargement.

19. A method according to claim 1, wherein the compaction pressure is chosen within the range of 300 to 900 MPa.

20. A method according to claim 1, wherein the shrinking and sintering are carried out in one, two or more cycles or wherein when carrying out the shrinking and sintering in sintering equipment temperature is increased a number of degrees per minute.

21. A product intended as a component in a dental application, where the product cooperates with members in the form of implants, attachment parts for implants, bones, dentine, or tooth remnants and made from worked or sintered powder material, wherein the powder material comprises titanium powder material deformed by compaction and sintered to a porosity of at most about 6 percent by volume.

22. A product according to claim 21, wherein the compacted and sintered material is homogeneous and ductile.

23. A method of use comprising installing the product of claim 21 in the human body.

24. The method of use of claim 23, wherein the product is cap-like and self-supporting.

25. A product according to claim 21, wherein the product has a configuration which has essentially a cap-like character and is conically tapering from its free end.

26. A product according to claim 21, wherein the product is thin-walled and has a wall thickness within the range of 400 to 600 μm.

27. A product according to claim 21, wherein the product has a precision fit on inner or outer shapes of the product of about 20 μm.

28. A product according to claim 21, wherein the product forms a self-supporting structure whose strength properties correspond to those of a conventional product for a dental application or other application in the human body.

29. A product according to claim 21, wherein an inner shape of the product is designed so that the product can be applied with an intermediate gap of 100 to 400 μm.

30. A product according to claim 21, wherein the product has a degree of compaction which allows the product to be worked by cutting tools when producing an outer shape of the product.

\* \* \* \* \*